United States Patent
Wilzbach et al.

(10) Patent No.: US 9,554,701 B2
(45) Date of Patent: Jan. 31, 2017

(54) ARTICLE FOR USE IN AN OCT-METHOD AND INTRAOCULAR LENS

(71) Applicant: CARL ZEISS MEDITEC AG, Jena (DE)

(72) Inventors: Marco Wilzbach, Stuttgart (DE); Martin Hacker, Jena (DE); Christoph Hauger, Aalen (DE)

(73) Assignee: CARL ZEISS MEDITEC AG, Jena (DE)

( * ) Notice: Subject to any disclaimer, the term of this patent is extended or adjusted under 35 U.S.C. 154(b) by 282 days.

(21) Appl. No.: 14/265,654

(22) Filed: Apr. 30, 2014

(65) Prior Publication Data

US 2014/0233037 A1    Aug. 21, 2014

Related U.S. Application Data

(63) Continuation of application No. 12/858,216, filed on Aug. 17, 2010, now Pat. No. 8,740,380.
(Continued)

(30) Foreign Application Priority Data

Aug. 17, 2009   (DE) .................. 10 2009 037 708

(51) Int. Cl.
*A61B 3/14*        (2006.01)
*A61B 3/00*        (2006.01)
(Continued)

(52) U.S. Cl.
CPC ............. *A61B 3/102* (2013.01); *A61B 5/0066* (2013.01); *A61B 17/30* (2013.01);
(Continued)

(58) Field of Classification Search
CPC ....... A61B 3/102; A61B 5/0066; A61B 17/30; A61B 19/5202; A61B 90/30; A61F 2/1613; A61F 2/16; B29D 11/023; G01B 9/02091; G02B 5/08; G02B 5/22; B82Y 20/00
(Continued)

(56) References Cited

U.S. PATENT DOCUMENTS

| 4,909,690 A | 3/1990 | Gapp et al. |
| 6,130,672 A | 10/2000 | Yamazaki et al. |

(Continued)

FOREIGN PATENT DOCUMENTS

| DE | 10 2005 028 882 A1 | 1/2007 |
| DE | 10 2005 041 271 A1 | 3/2007 |
| DE | 10 2007 019 680 A1 | 5/2008 |

OTHER PUBLICATIONS

Choma et al., "Sensitivity advantage of swept source and Fourier domain optical coherence tomography", Optics Express, 2003; 11(18): 2183-2189; retrieved from the Internet: <http://web.mit.edu/2.717/www/swept_oct_izatt_03.pdf>.
(Continued)

*Primary Examiner* — Bumsuk Won
*Assistant Examiner* — Collin X Beatty
(74) *Attorney, Agent, or Firm* — Patent Portfolio Builders PLLC (57) ABSTRACT

An article for use in an OCT method, the article comprising a solid substrate and nanoparticles dispersed in or on the substrate in at least one light transmissive portion of the article such that the nanoparticles result in an increased extinction of the light transmissive portion along a transmission direction of the light transmissive portion compared to the substrate being free of nanoparticles. The extinction of the light transmissive portion along the transmission direction is less than 6, wherein the extinction is defined as a negative decadic logarithm of a ratio of an intensity of light
(Continued)

which is transmitted through the light transmissive portion to an intensity of light which is incident on the light transmissive portion, wherein the light is in at least one of a visible and a near infrared wavelength range.

32 Claims, 6 Drawing Sheets

Related U.S. Application Data (60) Provisional application No. 61/234,778, filed on Aug. 18, 2009.

(51) Int. Cl.

| | | |
|---|---|---|
| *A61F 2/16* | (2006.01) | |
| *A61B 18/18* | (2006.01) | |
| *A61B 17/50* | (2006.01) | |
| *A61B 3/10* | (2006.01) | |
| *A61B 19/00* | (2006.01) | |
| *A61B 5/00* | (2006.01) | |
| *A61B 17/30* | (2006.01) | |
| *B29D 11/02* | (2006.01) | |
| *G01B 9/02* | (2006.01) | |
| *G02B 5/08* | (2006.01) | |
| *G02B 5/22* | (2006.01) | |
| *B82Y 20/00* | (2011.01) | |

(52) U.S. Cl.
CPC ........ *A61B 19/5202* (2013.01); *A61F 2/1613* (2013.01); *B29D 11/023* (2013.01); *G01B 9/02091* (2013.01); *G02B 5/08* (2013.01); *G02B 5/22* (2013.01); *A61B 90/30* (2016.02); *A61F 2/16* (2013.01); *B82Y 20/00* (2013.01)

(58) Field of Classification Search
USPC ........ 356/479, 445, 450; 430/270.1; 604/20; 606/4, 210; 623/6.11; 351/200, 206, 246; 977/773, 904
See application file for complete search history.

(56) References Cited

U.S. PATENT DOCUMENTS

| | | |
|---|---|---|
| 8,357,196 B2 | 1/2013 | Jain et al. |
| 2006/0177379 A1 | 8/2006 | Asgari |
| 2006/0228011 A1 | 10/2006 | Everett et al. |
| 2007/0009431 A1 | 1/2007 | Maschke |
| 2007/0269488 A1 | 11/2007 | Ravi |
| 2008/0117432 A1 | 5/2008 | Reimer et al. |
| 2008/0117503 A1 | 5/2008 | Reimer et al. |
| 2008/0117504 A1 | 5/2008 | Reimer et al. |
| 2008/0269884 A1 | 10/2008 | Vannoy |
| 2008/0304144 A1 | 12/2008 | Reimer et al. |
| 2012/0225298 A1* | 9/2012 | Graham ............ B82Y 30/00 428/412 |

OTHER PUBLICATIONS

Glucksberg et al., "Novel nanoparticles for contrast enhancement optical coherence tomography in doppler", Invest Ophthalmol Vis Sci 2002;43; E-Abstract 4378; retrieved from the Internet: http://abstracts.iovs.org/cgi/content/abstract/43/12/4378>.

Lee et al., "Engineered microsphere contrast agents for optical coherence tomography", Optics Letters, Sep. 1, 2003; 28(17): 1546-1548; retrieved from the Internet: <http://biophotonics.illinois.edu/publications/biophotonics_current/engineeredmicrospherecontrastagents.pdf>.

Leitgeb et al., "Performance of fourier domain vs. time domain optical coherence tomography", Optics Express, Apr. 21, 2003;11(8):889-894; retrieved from the Internet: <http://stuff.mit.edu/afs/athena/course/2/2.717/www/fd_vs_td_oct_fercher_03.pdf>.

Low et al., "Technology Insight: optical coherence tomography—current status and future development", Nat Clin Pract Cardiovasc Med. Mar. 2006;3(3): 154-162; quiz 172.

Van Velthoven et al., "Recent developments in optical coherence tomography for imaging the retina" og Retin Eye Res. Jan. 26, 2007(1):57-77, Epub Dec. 8, 2006 [Abstract Only}.

Vollath, "Nanomaterials", Wiley-VCH Verlag, Weinheim, 2008, ISBN 978-3-527-31531-4, pp. 145-149.

Wilzbach et al., "Contrast enhancement of optical coherence tomography" CG-EA/Nanoparticles, Mar. 20, 2009, pp. 1-5.

Zagaynova et al., "Constrasting properties of gold nanoparticles for optical coherence tomography: phantom, in vivo studies and Monte Carlo simulation", Phys. Med. Biol. 2008; 53(18):4995-5009.

Office Action of German Application No. 10 2009 037 308.5, dated Feb. 24, 2010 as well as an English translation thereof, 12 pages total.

* cited by examiner

ARTICLE FOR USE IN AN OCT-METHOD AND INTRAOCULAR LENS

CROSS-REFERENCES TO RELATED APPLICATIONS

This application is a continuation of U.S. patent application Ser. No. 12/858,216, filed on Aug. 17, 2010, entitled "Article for Use in an OCT-Method and Intraocular Lens," which is related to, and claims priority from, U.S. Provisional Patent Application No. 61/234,778, filed on Aug. 18, 2009, entitled "Article for Use in an OCT-Method and Intraocular Lens," and German Patent Application No. 10 2009 037 708, filed Aug. 17, 2009, entitled "ERZEUGNIS ZUR VERWENDUNG IN EINEM OCT-VERFAHREN UND INTRAOKULARLINSE," the contents of which are hereby incorporated by reference in their entirety.

FIELD OF THE INVENTION

The present invention relates to an article for use in an OCT method and an intraocular lens. The present invention further relates to a system, which comprises an OCT system and an article for use in an OCT method and/or an intraocular lens. Furthermore, the present invention relates to methods, in which optical coherence tomography (OCR) is applied by using an article in an OCT method and/or an intraocular lens. In particular, the present invention relates to an article for use in an OCT method, wherein the article comprises a substrate, in which nanoparticles are dispersed.

BACKGROUND OF THE INVENTION

Optical coherence tomography (OCT) is an optical method for determining structural information within a volume portion of an object.

Recently, surgical procedures are increasingly conducted by using OCT to image the surgical area. For such surgical operations, which are conducted by using OCT, there are presently articles, like surgical instruments and implants available, which however are only of limited practical use. These articles are mostly manufactured of metal and therefore structures of the examination area, which are located downstream of the article are covered by the article. Also, known articles for in vitro investigations (i.e. outside of a living organism) conducted by using OCT are only of limited practical use.

Today, OCT is widely applied in eye examination procedures. In particular, OCT may be applied during cataract surgery, in which the lens after being emulsified is removed from the capsular bag and an intraocular lens is implanted. However, it has shown that the intraocular lenses, which are presently available, are only of limited use for being observed by OCT.

Therefore, it is an object to provide an article, which is suitable for use in an OCT method. A further object is to provide a system and a method, which improves imaging of such an article by using OCT.

It is a further object to provide an intraocular lens which makes it possible a more successful cataract surgery. A further object is to provide a system and a method, which comprises or applies such an intraocular lens, wherein OCT is used for generating images.

SUMMARY OF THE INVENTION

According to an embodiment, there is provided an article for use in an OCT method, wherein the article comprises a solid substrate. Nanoparticles are dispersed in the substrate or are dispersed on the substrate, wherein the nanoparticles are located in a light transmissive portion of the article, such that the nanoparticles result in an increased extinction of the light transmissive portion along a transmission direction of the light transmissive portion compared to the substrate being free of nanoparticles. The extinction of the light transmissive portion along the transmission direction is less than 6, in particular less than 5, further in particular less than 4, further in particular less than 3, further in particular less than 2, wherein the extinction is defined as a negative decadic logarithm of a ratio of the intensity of light, which is transmitted through the light transmissive portion of the article along the transmission direction to the intensity of light, which is incident on the article, wherein the light is in at least one of the visible and near infrared wavelength range.

The substrate is made of a solid material. In other words, the substrate is in a non-liquid and non-gaseous state. The solid substrate may be a plastic and/or an elastic material. In particular, the substrate may have a hardness of at least 1 according to Mohs scale.

For example, the substrate may be made of at least one of glass, plastics, a polymer material, a synthetic thread.

The substrate, when being free of nanoparticles (i.e. when the substrate is measured without any nanoparticles), may have an extinction in the light transmissive portion along the transmission direction of below 2, in particular of below 1, further in particular of below $\log_{10} 2$, wherein the light is in at least one of the visible and near infrared wavelength range.

The extinction is a measure for a degree of attenuation of an intensity of light, which is transmitted trough the at least one light transmissive portion. The extinction of the intensity of light, which is transmitted through the at least one light transmissive portion may be caused by different physical processes. These physical processes comprise for example adsorption, scattering, fluorescence excitation, etc. Therefore, an increase of the extinction of a substrate may not necessarily be coupled to an increase of the reflectivity of the substrate. For determining the extinction, light in at least one of the visible and the near infrared wavelength range is directed onto the at least one light transmissive portion of the article, along a transmission direction, and transmitted through the at least one light transmissive portion. After transmission of the light through the light transmissive portion, substantially along the transmission direction, the intensity of the light is determined. Thereafter, a ratio of the light intensity, which is transmitted through the article to a light intensity, which is incident on the article is determined.

The extinction is a property of the article, which is dependent in particular on the transmission direction, the structure and material along the transmission direction within the at least one light transmissive portion of the article. Furthermore, the extinction also depends on a wave length of the used light. The extinction may be considered as an integral parameter along a path of the light, which is transmitted through the article along the transmission direction. The intensity $I_t$ of the transmitted light is related to the intensity $I_e$ of the incident light according to Lambert's law:

$$I_t = I_e \cdot \exp(-\tau \cdot D), \qquad \text{Equation (1)}$$

wherein the parameter $\tau$ denotes the linear extinction coefficient in the at least one light transmissive portion of the article along the transmission direction, and wherein D denotes a length of a path through the at least one light transmissive portion along the transmission direction. The extinction is given by the following equation:

$$\text{extinction} = -\log_{10}\left(\frac{I_t}{I_e}\right) \quad \text{Equation (2)}$$

Hence, the following equation results, being the relationship between the extinction and the linear extinction coefficient τ:

$$\text{extinction} = \frac{1}{\ln 10} \cdot \tau \cdot D \quad \text{Equation (3)}$$

The extinction is measured by using light in the visible and/or near infrared wavelength range. The intensity $I_t$ of the transmitted light and the intensity $I_e$ of the incident light are measured. Light in the visible wavelength range comprises electromagnetic waves having wavelengths of between 400 nm to 700 nm. Light in the near infrared wavelength range comprises electromagnetic wavelengths, which are longer than 700 nm and range up to about 2.5 μm, in particular up to about 1.3 μm. In one or more portions of the visible and near infrared wavelength range, the extinction may be below 6, in particular below 5, further in particular below 4 or 3 in the at least one light transmissive portion of the article and along the transmission direction. The extinction does not have to be between these limits in all portions of the visible and near infrared wavelength range.

In case the substrate being free of nanoparticles is transmitted by light in the visible and/or near infrared wavelength range along a length D, which is parallel to the transmission direction, the extinction may be below $\log_{10} 2$. Hence, at least half of the intensity of the incident light is transmitted through the substrate in case the substrate comprises no or a negligibly small amount of nanoparticles along the path of the transmitted light. Thereby, the pure substrate is substantially transparent for light in the visible and/or near infrared wavelength range.

The substrate may be considered as a basic structure or matrix wherein nanoparticles are dispersed in at least one light transmissive portion. The nanoparticles may be dispersed in a volume of the light transmissive portion of the substrate and/or arranged on a surface of the substrate. The presence of the nanoparticles in the at least one light transmissive portion results to an increased extinction in this portion, compared to the same portion being void of nanoparticles (i.e. where only the substrate is present). The increase of extinction which is caused by the presence of the nanoparticles may be calculated in particular from the arrangement of the nanoparticles and their properties. This is discussed further below. The increased extinction may assume a value of up to 5. In particular, the increased extinction may assume a value of up to 6. At the limit of 6 of the extinction, in the at least one transmissive portion of the article, the ratio of the intensity of the transmitted light to the incident light amounts to $10^{-6}$. Further in particular, the increased extinction may assume a value of up to 4. The increased extinction may also assume values of up to 3.

The substrate may have a hardness of a least 1 according to Mohs scale. The Mohs scale of hardness comprises degrees of hardness of 1 to 10 with 1 being the softest and 10 the hardest. Specimen with a higher hardness scratch other specimen with a lower Mohs hardness. One example of a specimen with a Mohs hardness of 1 is talc, which can be scraped by fingernails. The substrate of the article may have a hardness of greater than 1, greater than 2, greater than 3 greater than 4, greater than 5, greater than 6 or greater than 7. The substrate is therefore no liquid, but a solid material, which is composed of elements or molecules in a substantially stable configuration relative to each other.

According to an embodiment, a reflectivity in at least one reflective portion of the light transmissive portion is increased caused by the presence of nanoparticles by at least 0.1%, in particular by at least 1%, further in particular by at least 10%, further in particular by at least 50%, further in particular by at least 100%, further in particular by at least 500%, further in particular by at least 5000%.

The term reflectivity may be a portion of light, which is reflected by the reflective portion of the article in a direction, which is substantially reverse to the direction of incidence on the articles, wherein the direction of incidence is parallel to the transmission direction.

Hence, the reflected light, which contributes to the measurement of the reflectivity, propagates substantially in a direction reverse to the direction of incidence, wherein the propagation direction of the reflected light may deviate from the reverse incidence direction by up to 10 degrees, in particular by up to 5 degrees, further in particular by up to 2 degrees. The increase in reflectivity by for example 10% in the at least one portion compared to the substrate void of nanoparticles is caused by the presence of nanoparticles. The increase of reflectivity this portion preferably causes an increased signal in case the signal is imaged using an OCT system. Therefore, dispersing the nanoparticles into a volume or onto a surface of the substrate, the article which is imaged by OCT can be made visible.

According to an embodiment, the article comprised a reflective portion within the light transmissive portion, wherein a reflectivity of the reflective portion along the transmission direction is greater than $10^{-10}$, in particular greater than $10^{-9}$, further in particular greater than $10^{-7}$ or greater than $10^{-6}$ or greater than $10^{-5}$ wherein the light is in at least one of the visible and near infrared wavelength range.

The wavelengths, which are used to define the extinction of the light transmissive portion of the article and the wavelengths, which are used to define the reflectivity of the reflective portion of the article may be at least in part identical.

The reflectivity of the reflective portion may be defined by the following equation:

$$\text{reflectivity} = \left(\frac{I_r}{I_e}\right), \quad \text{Equation (4)}$$

wherein $I_e$ is the intensity of the light, which is incident on the article, wherein the light is measured after it has left the OCT system and before it enters the article. $I_r$ is the intensity of light, which is reflected by the reflective portion of the article, wherein the intensity is measured after the light has left the article and before it enters the OCT system.

The reflectivity is measured, along the transmission direction, of the light transmissive portion. In other words, $I_e$ is the intensity of light of an incident light beam, which is parallel to the transmission direction and $I_r$ is the intensity of the reflected light beam, which is antiparallel (i.e. has an opposite direction) to the transmission direction.

The reflectivity of a reflective portion of the transmissive portion may be measured by means of an OCT system. For example, by knowing the sensitivity of the OCT system, it may be possible to measure a value of a reflectivity of a portion of an object which has been scanned by the OCT measuring light. The sensitivity of an OCT system may be determined for example by theoretical calculations or by comparative measurements.

The reflectivity of the reflective portion is therefore a property of the article, which may be measured by scanning the reflective portion with an OCT system.

In case the reflective portion is not located on the surface, the reflectivity of the reflective portion may also include the extinction of the light, which is cause by traveling from the surface of the article to the reflective portion and further by traveling back to the surface of the article after having been reflected at the reflective portion.

According to an embodiment, the nanoparticles which are dispersed in the at least one light transmissive portion, cause an increase in extinction of at least $10^{-4}$ relative to the substrate when being free of nanoparticles. In other words, the nanoparticles cause an increase by a factor of $10^{-4}$ relative to the substrate when being free of nanoparticles. In particular, the increase in extinction may be of at least $10^{-3}$, further in particular of at least $10^{-2}$, further in particular of at least $10^{-1}$.

The increased extinction, may be accompanied for example by an increased reflectivity, which facilitates a detection of the article by an OCT system.

According to an embodiment, the nanoparticles have an extent of between 1 nm and 100 μm, in particular of between 2 nm and 500 nm, further in particular of between 10 nm and 200 nm. The nanoparticles may have shapes, such as substantially spherical, ellipsoidal, and therefore may have different diameters along different directions. The extent of a nanoparticle may be defined as the greatest diameter, width or length of the nanoparticle. A minimal diameter of the nanoparticles may be in the range between 1 nm and 100 μm in particular between 2 nm and 500 nm or between 10 nm and 200 nm. Nanoparticles of this extent are commercially available.

According to an embodiment, the nanoparticles are made of a material, which comprises a metal, in particular gold, silver, titanium, copper, cobalt, nickel, and/or iron; silicon and/or oxygen. In particular, the metal may be deposited on a shell, which surrounds a core, wherein the core may comprise silicon. In other words, the nanoparticles may comprise an inert metal, such as gold, which may be arranged on its surface. Thereby, the nanoparticle may be biocompatible.

According to an embodiment, the nanoparticles may be dispersed in a volume region of the substrate, additionally or alternatively, the nanoparticles are dispersed on a surface region of the substrate.

In case the at least one portion, where nanoparticles are dispersed is a volume region, the concentration of the nanoparticles may be defined as the number of nanoparticles in a unit volume of the volume region article. In case the at least one light transmissive portion, in which the nanoparticles are dispersed is a surface region, the concentration of the nanoparticles may be defined as a number of nanoparticles per unit surface area.

According to an embodiment, concentrations of nanoparticles in two subportions of the portion, in which the nanoparticles are dispersed, differ by at least a factor of two.

Concentrations of nanoparticles may be greater in subportions having a smaller transmission path length, compared to subportions having a longer transmission path length, wherein the transmission path lengths of the subportions are oriented parallel to the transmission direction.

According to an embodiment, the nanoparticles may be dispersed in a volume or on a surface of the article such that an article of transmission path and concentration of nanoparticles is substantially constant. Thereby, an article may be made visible by imaging with an OCT system, independent from its shape.

According to an embodiment, at least 80% of the nanoparticles are arranged on a surface of the substrate. Arranging the majority of the nanoparticles on the surface of the substrate makes it possible to image the surface of the substrate by an OCT system, wherein the surface spatially limits the article. Such a spatially limiting surface and hence the surface of the article may therefore be better determined by an OCT system, thereby enabling improved positioning of the article within or close to an object, which is to be examined.

According to an embodiment, the extent of the at least one portion, in which the nanoparticles are dispersed, along at least one transmission direction of light is smaller than 20 mm, in particular smaller than 10 mm, further in particular smaller than 2 mm. The extent of the at least one portion, in which the nanoparticles are dispersed is denoted with the symbol D.

According to an embodiment, the substrate is made of a material, which comprises glass and/or plastic, in particular a polymer. Thereby, the substrate may be manufactured in an easy way.

According to an embodiment, the article is a manipulator, in particular tweezers, scalpel, a tube, and additionally or alternatively an implant, in particular an intraocular lens or a surgical thread. The tweezers may comprise jaws, which are movable relative to each other, such that tissue may be grasped by closing the jaws. The at least one portion, in which the nanoparticles are dispersed may be located at least partly within at least a grasping portion of the jaws. The scalpel may comprise a blade, which is arranged at the substrate. The tube may be designed as suction tube. The suctioning tube may be designed such that liquid is suctionable from an examining region or a surgical area.

According to an embodiment, the article comprises a surgical thread, comprising in particular Prolene having a thickness of less than 100 μm, in particular of less than 30 μm. Such a surgical thread may be used for eye surgery, in particular for a surgery, where the thread is inserted into the Schlemm's canal of the human eye. By using an OCT system in combination with the surgical thread, it is possible to determine the geometry of the Schlemm's canal when the surgical thread has been inserted into the Schlemm's canal. Furthermore, by inserting the thread into the Schlemm's canal, the Schlemm's canal can be extended in a defined way.

According to an embodiment, an article as described above is used in an OCT method for imaging the article. Due to an increased reflectivity of the article in the at least one light transmissive portion because of the presence of the nanoparticles, the article can better be imaged by an OCT system compared to commonly available articles.

According to an embodiment, a system is provided, having a light source for emitting an OCT measuring light beam along a path of OCT measuring light to an object and a detector for detecting the OCT measuring light returning from the object; and further comprising an article as described above. The article is arrangeable in the path of the OCT measuring light. The light source may comprise light having wavelengths in the visible and/or near infrared wavelength range, wherein a bandwidth of the light source is configured such that a coherence length of the light emitted by the light source ranges between several micrometers and several ten micrometers. A part of the OCT measuring light beam which is emitted from the light source is directed along a path of OCT light which may comprise mirrors, lenses and/or fiber optics to an object. The light penetrates into the object along a penetration depth. A part of the penetrated measuring light is reflected within the object depending on a reflectivity of the object. A second part of the light, which is emitted by the light source is reflected at a reference surface. The first part and the second light are interferometrically superposed. The superposed light is detected by a detector and converted into electrical signals, which represent intensities of the detected superposed light. Due to the comparable short coherence length of the OCT measuring light, constructive interference can only be observed in case the difference of the optical path of the OCT measuring light which travels towards and returns from the object and the OCT measuring light of the second part which is reflected by the reference surface is less than the coherence length of the OCT measuring light.

Different embodiments may comprise different variants of the OCT system. The different variants of the OCT system may be different in the way, in which structural information is scanned along a depth direction (axial direction), and also in the way in which the superposed light is detected. According to time domain OCT (TD-OCT), the reference surface, at which the second part of the light which is emitted by the light source is reflected, is displaced for obtaining structural information of the object from different depths. In this case, an intensity of the superposed light may be detected by a photo detector.

Also in frequency-domain-OCT (FD-OCT), the second part of the OCT measuring light, which is emitted by the light source is reflected at the reference surface. However, the reference surface does not have to be displaced for obtaining structural information from different depths within the object. Rather, the superposed light is split by a spectrometer into spectral portions. The spectral portions may for example be detected by a position sensitive detector. Structural information of the object along the depth direction may be obtained by a Fourier transform of the measured spectrum of the superposed light (Fourier transform OCT).

Another variant of FD-OCT is swept source OCT (SS-OCT). A spectrum of superposed light is recorded successively, wherein a mean wavelength of a narrow band of illumination light is varied continuously and, at the same time, the superposed light is detected by using a photo diode.

The article, in which nanoparticles are dispersed in at least one light transmissive portion thereof is arrangeable in the OCT measuring light and therefore imagable. Since the article may have in the light transmissive portion in which nanoparticles are dispersed an extinction of less than 5, reflecting structures, which are located downstream of the article are imagable by an OCT system having a sensitivity of 100 dB, wherein the light is transmitted through the article two times.

According to an embodiment, the extinction of the portion in which nanoparticles are dispersed, is small enough, such that reflecting structures are detectable, which are located downstream of the portion in which nanoparticles are dispersed. Thereby, by choosing the material, the geometric shape, the extent and the concentration of the nanoparticles, the extinction of the portion in which nanoparticles are dispersed may be adjusted such that the portion in which the nanoparticles are dispersed and also the structures which are located downstream are imagable with the OCT system.

According to an embodiment, the following relationship holds between a reflectivity of a reflective portion which is in the light transmissive portion, and the sensitivity of the OCT system:

$$-10*\text{Log}_{10}(\text{reflectivity}) < \text{sensitivity},$$

wherein the light is in at least one of the visible and the near infrared wavelength range.

According to an embodiment, the system further comprises a processing system for determining data, which represent a structure of the object from the OCT measuring light, which is detected by the detector and depending on the optical path along which the OCT measuring light has traversed the article. An optical path through the article which is transmitted by light corresponds to a traveled path and an index of refraction n of the article in the light transmissive portion. The index of refraction n of the article may be greater than 1. At low concentrations of the nanoparticles, the index of refraction of the article may be approximately the index of refraction of the substrate. In general, the index of refraction depends on the wavelength of the OCT measuring light. The index of refraction of vacuum is exactly 1 for each of the used wavelengths. For solid materials, such as glass or plastics, the index of refraction for visible or near infrared light ranges between 1.2 and 1.9. The optical path of the OCT measuring light, along which the light is transmitted through the article is therefore greater than the geometrical path through the article which is transversed by light. For correcting the thereby generated artifacts to structural information of portions, which are located downstream of the article which is traversed by light, the measured portion of the structures, which are imaged by the OCT system and which are located downstream of the article which is traversed by light are shifted by twice the difference between the optical path through the article which is transmitted by light and the geometrical path through the article which is transmitted by light. Thereby, corrected structure information of the object is obtained.

According to an embodiment, there is provided a method, comprising: illuminating an object with an OCT measuring light along a path of OCT measuring light; arranging one of the above described articles in the OCT measuring light; detecting OCT measuring light returning from the object and the article; and determining of data representing a structure of the object based on the detected OCT measuring light.

According to an embodiment, there is provided a method for manufacturing one of the above dispersed articles, wherein the method comprises geometrically shaping a substrate and dispersing nanoparticles into or onto the substrate. When nanoparticles are arranged substantially on a surface of the article, the geometrically shaping of the substrate may be performed before the nanoparticles are dispersed onto the substrate. The dispersing of nanoparticles onto the substrate may for example be performed by dipping the substrate into a solution with nanoparticles, by spraying the nanoparticles onto the substrate or by evaporating the nanoparticles close to the substrate. When the nanoparticles are located within the volume of the article substantially in the at least one portion in which the nanoparticles are dispersed, the dispersing of the nanoparticles in the substrate may be performed before the geometrical shaping of the substrate. In particular, the substrate may be in a liquid state, when the nanoparticles are dispersed therein. The nanoparticles may be distributed homogeneously or inhomogeneously within the substrate.

According to an embodiment, there is provided an intraocular lens, which comprises: an optical element, which is substantially transparent in the wavelength range; a mark which is arranged outside of the optical element in a radial direction, wherein the mark compared to the optical element has an increased reflectivity within the visible and/or near infrared wavelength range in at least a portion thereof by at least a factor of 2, in particular a factor of 10. The reflectivity of the mark and the optical element may refer to incident light, which is backscattered.

According to an embodiment, the reflectivity of the mark is at least $10^{-10}$. The reflectivity of the mark may be measured with light in at least one of the visible and infrared wavelength range. The reflectivity may be further in particular at least $10^{-9}$, further in particular at least $10^{-8}$, further in particular at least $10^{-7}$.

The mark is arranged outside the optical element in a radial direction, i.e. in a direction, which is oriented perpendicular to the optical axis. Thereby, the mark which may have a low transparency does not block out light, which is transmitted through the optical element along the optical axis. The higher reflectivity of the mark compared to the optical element results in an improved imaging of the mark by the OCT system.

The mark may in particular comprise a reflector foil. The mark may be structured such that it represents an identification of the optical properties of the intraocular lens, in particular of the optical element. For example, the mark may be structured such that the mark contains or comprises information which represents a refractive power of the spherical and/or toric optical element. A refractive power of a toric intraocular lens is intended to correct an astigmatic eye. In this respect, it is necessary that the intraocular lens is inserted into the capsular bag in a correct orientation, i.e. azimuthal orientation into the human eye for achieving a successful correction of the astigmatism. To this end, the toric intraocular leas comprises structures on its mark, which make it possible to determine the direction of the principal axis of the toric optical element like a lens. Thereby, a correct implantation of the intraocular lens is facilitated for correcting Hypermetropia, Myopia and/or astigmatism. Other information may be coded in the mark, such as a date of manufacturing the intraocular lens, a material of the intraocular lens or the like.

The intraocular lens may be implantable at different positions within the eye, such as within the natural capsular bag, in the anterior eye chamber or in the posterior eye chamber.

According to an embodiment, the optical element has a positive optical refracting power in the visible wavelength range, in particular between +18 diopters and +22 diopters. Thereby, an intraocular lens may function in particular as a substitute for a natural lens. When a bundle of parallel light beams is transmitted through the optical element along the optical axis in the visible wavelength range, the light rays are refracted towards the optical axis, such that light bundles which are parallel before being transmitted through the optical element are transformed into a convergent light bundle. A ratio of a light intensity which is transmitted through the optical element to a light intensity which is incident onto the optical element in the visible wavelength range is greater than 70% in particular greater than 90%.

The positive optical refracting power of the optical element may also range between +1 diopters and +8 diopters.

According to an embodiment, the optical element has a negative optical retracting power in the visible wavelength range, in particular ranging to −14 diopters.

The intraocular lens may be used as a phakic lens such as a posterior chamber intraocular lens (implanted contact lens, ICL) which is implanted between the iris and the natural lens in the sulcus or as an anterior chamber contact lens which is attached to the iris. For such intraocular lenses, the optical element may have an optical refractive power of less than 19 diopters or a negative refractive power.

According to an embodiment, the intraocular lens further comprises a holding element, which extends from inside to outside along a radial direction for holding the intraocular lens within the capsular bag of the eye. A size of the holding element is adapted to the size of the capsular bag. The holding element may in particular comprise two holding arms, which are arranged exactly or substantially opposite to each other and which extend from inside to outside along a radial direction, wherein the holding arms accommodate the optical element in a central portion of the intraocular lens between those holding arms.

According to an embodiment, the mark is arranged at the holding element. Thereby, the holding element serves two functions, which simplifies the construction of the intraocular lens.

According to an embodiment, the mark is arranged at a radial distance from the optical axis of between 1 mm and 10 mm, in particular between 2 mm and 7 mm, further in particular of between 3 mm and 6 mm. Thereby, the mark is arranged at a radial distance, which is greater than the radius of a maximal opening of the pupil of a human eye. In particular, the mark is arranged at smaller than the radius of the capsular bag of a human eye. In particular, the mark is arranged at a radial distance from the optical axis of the human eye such that the mark, when located downstream of the iris, may be imaged by an OCT system, without affecting the field of view of the human eye.

According to an embodiment, the mark comprises nanoparticles.

According to an embodiment, the intraocular lens comprises an article as described above for use in an OCT method, wherein the article has a substrate having a hardness of at least 1 according to the Mohs scale and an extinction of below $\log_{10}2$, wherein nanoparticles are dispersed in the substrate in at least one light transmissive portion of the article, such that the nanoparticles result in an increased extinction of below 5, in particular of below 6. The extinction is defined as a negative decadic logarithm of a ratio of the intensity of light which is transmitted through the article to light which is incident onto the article, wherein the light is in the visible or near infrared wavelength range.

According to an embodiment, there is provided a system, which comprises: an OCT system having a light source for emitting a beam of OCT measuring light along a path of the OCT measuring light towards the object and a detector for detecting OCT measuring light which returns from the object; and an intraocular lens, such as described above. The intraocular lens arrangeable in the path of OCT measuring light. Thereby, the intraocular lens, in particular the mark of the intraocular lens may be imaged by the OCT system.

In doing this, the intraocular lens may be implantable into the capsular bag for replacing the natural lens, or may be a posterior chamber lens, which may be fixed between the iris and the natural lens in the sulcus ciliaris, which is a circular groove between the root of the iris and the ciliary body. The intraocular lens may be fixed through a haptic of the intraocular lens.

According to an embodiment, there is provided a method, comprising: illuminating at least a portion of an eye with a beam of OCT measuring light along a path of OCT measuring light; arranging a mark of an intraocular lens as described above in the path of OCT measuring light; detecting at least a part of the OCT measuring light, which returns from the eye and the mark; imaging of the mark and least a portion of the eye by using the detected OCT measuring light.

The intraocular lens may be located within the capsular bag of the eye or may be an anterior chamber intraocular lens or a posterior chamber intraocular lens. Thereby, the intraocular lens according to an embodiment may be imaged in a medical examination. The medical examination may be carried out solely for the purpose of obtaining the optical properties of the intraocular lens by imaging the mark and decoding of the coded information on the mark. A similar medical examination may be carried out before, during or after an eye surgery. Thereby, for example, the correctness of the optical properties of the intraocular lens, such as a refractive power, or a correct orientation of the intraocular lens may be confirmed.

According to an embodiment, the method further comprises determining a location of the intraocular lens relative to the eye. The determining of the location of the intraocular lens relative to the eye may comprise a determining of the orientation of the optical axis of the optical element of the intraocular lens relative to an orientation of the optical axis of the human eye. Furthermore, in case the intraocular lens is also toric, the determining of the location of the intraocular lens relative to the eye may comprise a determining of the azimuthal orientation of a main axis of the intraocular lens. The direction of this main axis may be obtained from the information which is comprised by the mark of the intraocular lens.

BRIEF DESCRIPTION OF THE DRAWINGS

The forgoing as well as other advantageous features of the invention will be more apparent from the following detailed description of exemplary embodiments of the invention with reference to the accompanying drawings. It is noted that not all possible embodiments of the present invention necessarily exhibit each and every, or any, of the advantages identified herein.

FIG. 5b illustrates results of OCT measurements, which are obtained by measuring a surgical thread shown in FIG. 5a;

DETAILED DESCRIPTION OF THE INVENTION

In the exemplary embodiments described below, components that are alike in function and structure are designated as bar as possible by alike reference numerals. Therefore, to understand the features of the individual components of a specific embodiment, the descriptions of other embodiments and of the summary of the invention should be referred to.

Figure 1:
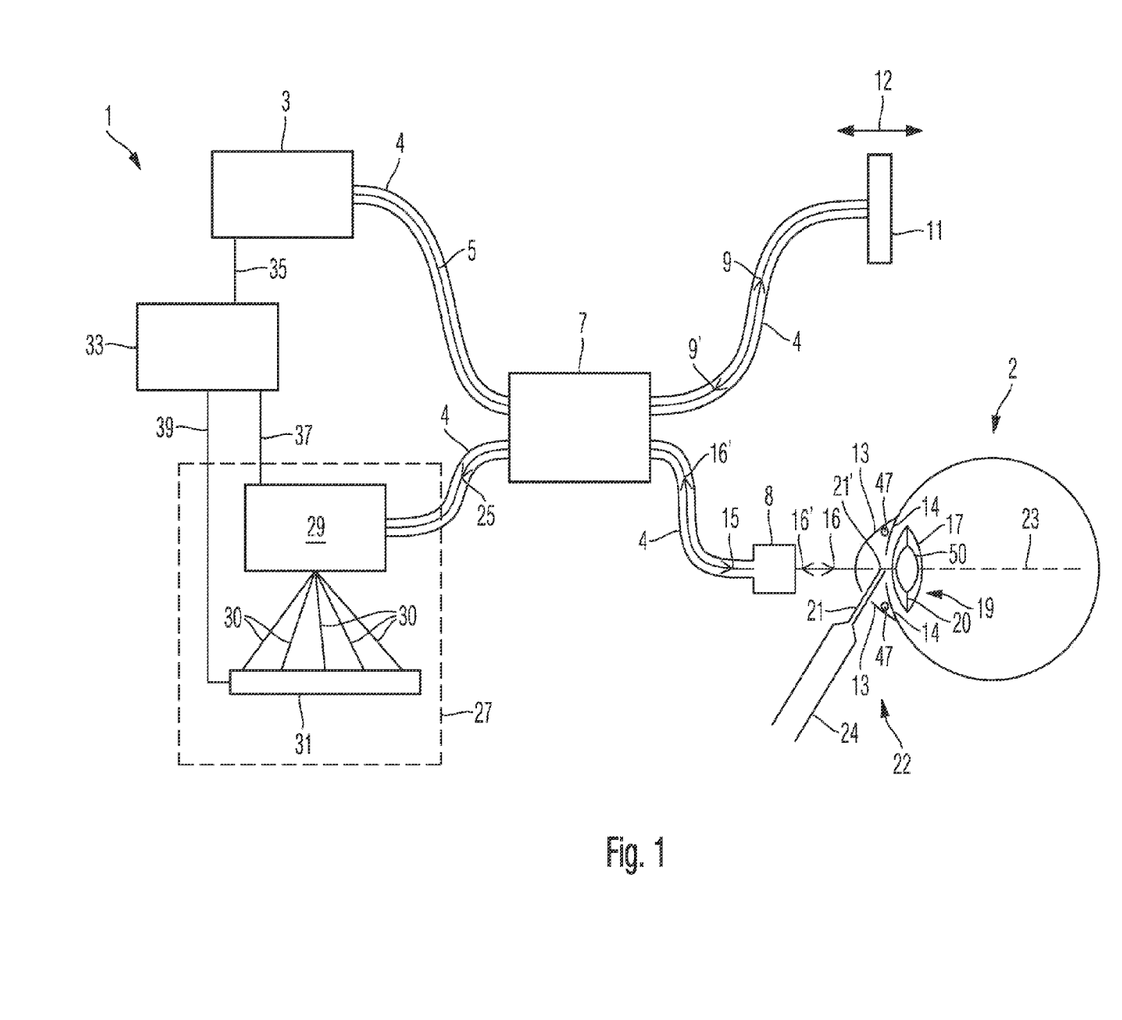
FIG. 1 illustrating an OCT system with an article and an intraocular lens according to an embodiment.

FIG. 1 schematically illustrates, in a simplified representation, an OCT system 1, which is used for examination of an human eye 2. In particular, the OCT system 1 may be used during an eye surgery, in particular during a cataract surgery. In the embodiment, which is schematically illustrated in FIG. 1, the OCT system is a Fourier domain OCT system (FD-OCT system), which is also referred to as spectral domain OCT system. Further embodiments comprise a swept source OCT system (SS-OCT system) or a time domain OCT system (TD-OCT system).

The FD-OCT system 1 comprises a light source 3, which generates measuring light 5 of a certain spectrum. The light source 3 comprises a super luminescent diode, which is designed such that OCT measuring light 5 is generated having a spectrum with a mean wavelength and a spectral width. The mean wavelength is about 1000 nm and has a spectral width of 20 to 30 nm. Alternatively, instead of using a super luminescent diode, the light source 3 may comprise a white light source and spectral filters, which are arranged in the path of OCT measuring light for approximately providing the above described spectrum. Through the optical fiber 4, the OCT measuring light 5 which is generated by the light source 3 is guided to the divider/coupler 7. The fiber optic divider/coupler 7 is configured such that OCT measuring light 5 is divided into two light portions 9 and 15. Light portion 9 is guided to a reflecting reference surface 11 by an optical fiber 4, at which the light portion 9 is reflected to constitute the light portion 9'. The reference surface 11 is disposable in directions which are indicated by double arrow 12. Thereby, a path length, which is traveled by light portions 9 and 9' is variable.

The other light portion 15 of the OCT measuring light 5 is guided by an optical fiber 4 to a scanner 8 having an illumination optical system. The scanner 8 including the illumination optical system is designed such that a focused beam of OCT measuring light 16 is formed having a defined cross-sectional extent in the examination area (i.e. an object region) of about 10 to 50 µm. The scanner 8 having the illumination optical system may also be designed such that a beam of measuring light 16 is formed, which consists of parallel light beams, in particular, for investigating a posterior portion of the eye, such as the retina.

The scanner 8 including the illumination optical system is further designed such that the bundle of OCT measuring light 16 is laterally guided over the examination area of the human eye 2. For this purpose, the scanner 8 may comprise one or more mirrors, which are pivotable about different axes.

The bundle of OCT measuring light 16 interacts with structures of the human eye 2, such as the cornea 13, the iris 14, the capsular bag 17, the intraocular lens 19, in particular the mark 20 of the intraocular lens 19, and with the suction tube 21. The suction inlet 21' of the suction tube 21 is arranged close to the capsular bag 17. The interaction of the bundle of OCT measuring light 16 comprises different physical processes such as scattering, reflection and absorption. A portion of the incident bundle of OCT measuring light 16 is reflected into a substantially reverse direction (i.e. reverse to the direction of the incident light), captured by the scanner 8 and directed again into the optical fiber 4 as light 16'.

The light 16' carries structure information of the examination area of the eye into which the bundle of OCT measuring light 16 has been penetrated. Light 16' is guided to the fiber optic divider/coupler 7, where it is superposed on the light portion 9', which has been reflected at the reference surface 11. Thereby, superposed light 25 is formed. The superposed light 25 is guided via the optical fiber 4 to the spectrometer 27. The spectrometer 27 comprises a dispersion device 29 for spectrally dispersing the superposed light into spatially separated light portions 30. Each of the light portions 30 comprises light waves having wavelengths of a certain wavelength range. The wavelength ranges of different light portions may be different. The spatially separated light portions 30 are detected by a position sensitive detector 31, which comprises a plurality of pixels for separately detecting intensities of different spatially separated light portions 30 and for generating electrical signals.

The electrical signals are led via signal line 39 to a control and processing system 33, which is designed such that the electrical signals are processed and date representing a structure of the examination area of the eye are determined. Namely, the intensities of the detected spectral light portions 30 represent a spectrum of the superposed light 25. From the spectrum of superposed light 25, structure information along a depth direction 23 is determinable after having applied background subtraction, spectral resampling and determining of a Fourier transform. The control and processing system 33 may be designed such that via a signal line 35, a change in the characteristics of the light source 3 in view of its spectrum is controlled. The control and processing unit may further be designed such that via a signal line 37, a dispersion strength of a dispersion device 29 is varied. From data which represents the structure of the examination area of the eye 2, an image of the examination area of the eye 2 may be obtained, which may be displayed on a monitor (not illustrated). This representation may comprise for example a volumetric view or a cross-sectional view of the object.

Embodiments provide articles, which may be applied during an examination or a surgery in which an OCT system 1 is used. On the one hand, the articles have a suitable reflectivity for being imaged by the OCT system 1, on the other hand, the bundle of OCT measuring light 16 is attenuated by the extinction of the article only such that anatomical structures of the eye 2 which are located downstream of the article are detectable and hence imagable by the OCT system 1.

The suction tube 21, which is illustrated in FIG. 1, comprises nanoparticles which are disposed on it surface. Thereby, the signal of the suction tube 21 is increased which leads to an improved detection by the OCT system 1 compared to a suction tube 21 without any disposed nanoparticles. The suction tube 21 is comprised by a suction device 22, which is provided for suctioning off an emulsified natural lens from the capsular bag 17 during a cataract surgery. The suction device 22 may be designed in the form of a phaco handpiece for phacoemulsification. Thereby, a suctioning off of lens fragments may be performed in an integrated way with the phaco handpiece.

The surgeon approaches the suction device 22 and in particular the suction inlet 21' of the suction tube 21 to the location where the surgery is performed. Thereby, the suction inlet 21' is approached as close as possible to an incision, which is made at the capsular bag 17 for suctioning off an emulsified natural lens. The increase in contrast of the imaged suction tube 21 which is caused by the dispersed nanoparticles provides a facilitated positioning of the suction inlet 21' of the suction tube 21 for the surgeon.

Figure 2:
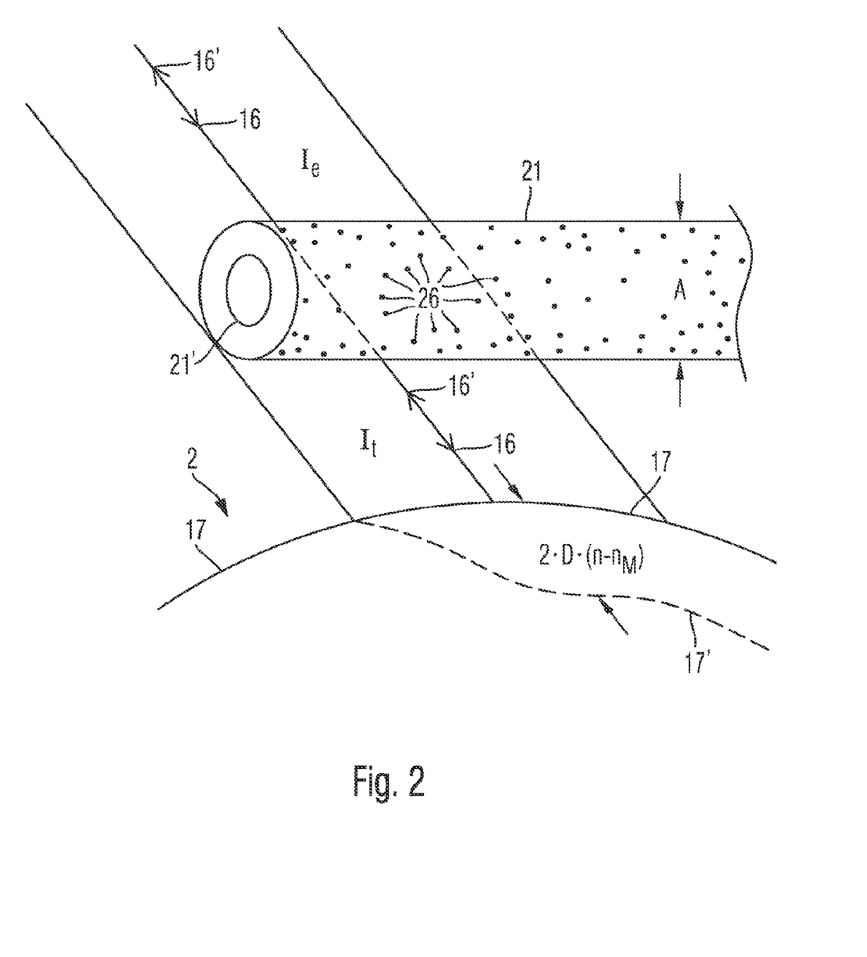
FIG. 2 illustrates an article which a suction tube according to an embodiment.

FIG. 2 schematically illustrates in more detail a portion of the suction tube 21 during an examination of the eye 2 by using the OCT system 1. The suction tube comprises a cylindrical substrate body having a diameter A of 2 mm and a wall thickness of about ⅕ mm. The diameter A may also have values of between 1 mm and 3 mm, and the wall thickness may also have values of between 1/20 mm to ½ mm. The cylindrical substrate body is made of glass or plastics. On the outer surface of the substrate body, there are located nanoparticles 26 which have a substantially constant surface concentration, i.e. the number of nanoparticles per unit area is substantially constant on the outer surface of the cylindrical substrate body. The nanoparticles have been deposited by dipping the substrate body into a solution of nanoparticles having a concentration of about $7 \times 10^8$ nanoparticles per ml. In other embodiments of the suction tube, the nanoparticles 26 are not only deposited on the surface of the substrate body, but rather are also located in the bulk of the cylindrical substrate body. Alternatively or additionally, the nanoparticles 26 may be deposited on the cylindrical inner surface of the suction tube 21.

During examination of the eye 2, the suction tube 21 is arranged in a beam path of the bundle of measuring light 16 of the OCT system 1, which is illustrated in FIG. 1. An intensity of the bundle of OCT measuring light 16, which is incident on the suction tube 21, is denoted as $I_e$. An intensity of the bundle of OCT measuring light, which transmits the suction tube 21 is denoted as $I_t$. Because of the presence of the nanoparticles on the surface of the cylindrical substrate body of the suction tube 21, the intensity $I_t$ of the transmitted OCT measuring light is smaller than the intensity $I_e$ of the incident OCT measuring light. The extinction, which is defined in equation (2) above may assume values of up to 10. Notwithstanding this significant attentuation of the intensity of the bundle of OCT measuring light 16 after having been transmitted through the suction tube 21, an anatomical structure of the eye 2, which is located downstream of the suction tube 21, (in this case the capsular bag 17) is imagable by the OCT system 1 illustrated in FIG. 1 because of the high sensitivity of the OCT system 1.

Generally, the sensitivity of an OCT system is defined as the minimal reflectivity of the probe arm of the interferometer at which the signal to noise ratio is 1. Instead of determining the minimal reflectivity of the probe arm, the maximum attenuation or extinction of the bundle of OCT measuring light at which an ideal mirror is detectable by an intensity $I_t$ of OCT measuring light. This results in the sensitivity which is given in decibel $$\text{sensitivity} = -10 \cdot \log 10\left(\frac{I_t}{I_e}\right) \quad \text{Equation (5)}$$

Sensitivities of modern OCT systems have been investigated in the publication "Performance of Fourier domain vs. time domain optical coherence tomography", R. Leitgeb et al, Optics Express. Vol. 11, No. 8, pages 889 to 894. It is possible to obtain a sensitivity of up to 108 dB. Using equations (2) and (5) and taking into account that the path goes through the article two times, and structures which are located downstream of the article have to be detectable, the maximum extinction is given by:

$$\text{max. extinction} = \frac{1}{2} \cdot \frac{1}{10} \cdot \text{sensitivity} \qquad \text{Equation (6)}$$

Thereby, in case the extinction of the suction tube 21 along a transmission direction, which is given by the direction of the incident handle of OCT measuring light 16, is smaller than the maximum extinction, which is defined in equation (6), in particular smaller than 5, a boundary layer or interface of the capsular bag 17 is detectable by the OCT system 1.

OCT measures light 16', which emanates from the examination area of the eye 2, which is located downstream of the suction tube 21, has covered an additional optical path $D \cdot (n-n_M)$. D denotes a thickness of the transmitted substrate material of the suction tube 21 having an index of refraction n on the way to and fro, and $n_M$ represents an index of refraction of the medium, which in this case the aqueous humor within the eye. Without a correction of structural data taking into consideration this additional optical path, the capsular bag 17 would be illustrated according to the dashed line 17'.

The control and processing system 33, however, is designed such that based on knowledge of the geometry of the suction tube 21, the refractive index of the suction tube 21 and the orientation and position of the suction tube 21, a correction is performed. Thereby, the capsular bag 17 which is erroneously depicted downstream of the suction tube 21 as contour 17', is displayed as corrected contour 17. This correction may be performed in a real space of the volume data set, for example by displacing pixel values according to the additional optical path of the OCT measuring light 16, 16' for portions of the object, which are located downstream of the suction tube 21.

Embodiments of an article, may have an index of refraction, which is adapted to a medium of the area of examination. In this case a correction as described above is not required. For example, the article may be made of plastics, having an index of refraction of about 1.3 to 1.4 in the wavelength range of the used OCT measuring light. A deviation of the index of refraction of the article from a mean index of retraction of the medium of the area of examination may be chosen to be smaller than the ratio of the resolution of the OCT system to the extent of the article of the portion through which the OCT light is transmitted.

Figure 3:
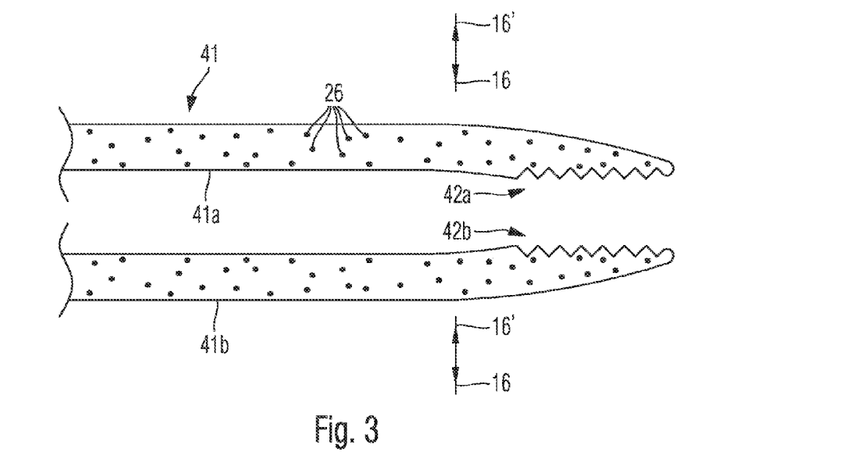
FIG. 3 illustrates an articles in the form of tweezers according to an embodiment.

FIG. 3 shows a further article 41, which may be used in a method by using the OCT system 1. The article is configured as tweezers made of glass or plastics. Nanoparticles 26 are dispersed in the volume.

Different embodiments of the article which are described in this application may comprise different nanoparticles or a mixture of different nanoparticles. The nanoparticles may comprise for example $AlO_3$, wherein the nanoparticles have an extent of between 100 nm and 100 μm. The nanoparticles may also comprise Au, wherein the nanoparticles have an extent of between 2 nm to 250 nm. The nanoparticles may also comprise Ag, wherein the nanoparticles have an extent of between 20 nm to 80 nm or of between 20 nm and 300 nm. Additionally or alternatively, the nanoparticles may comprise other metals and/or silicon. The nanoparticles may consist completely of metal or may comprise a core made of silicon or silicon oxide around which a shell of metal is formed. For given articles having a given geometry and a given substrate material, the extinction along any transmission direction of the articles may be calculated depending on a material, a shape, a size and a concentration of nanoparticles. In the calculation, the nanoparticles may be approximated by a sphere.

Since the scattering process of light at a homogenous sphere cannot be expressed analytically, numerical procedures such as Mie theory have to be applied for a given configuration of the article. The so-called Mie coefficients $a_n$ and $b_n$ are calculated for a given configuration of the article and given boundary conditions, for example by applying the program "MieCale" (Bernhard Michel) and/or "Mie Scattering Calculator" (Scott Prahl). Based on these Mie coefficients and based on the radius of the sphere of the nanoparticles, the efficiency of the extinction $Q_{ext}$ may be calculated for a given article. The calculation of the Mie coefficients is also based on the complex index of refraction $n = n_r - i \cdot n_i$ of the nanoparticles. By way of example, at a wavelength of 840 nm of the OCT measuring light, gold nanoparticles have a real index of refraction $n_r = 0.18$ and an imaginary index of refraction $n_e = 5.36$. The linear coefficient of extinction τ is related to the efficiency of extinction $Q_{ext}$ by the following equation:

$$\tau = \pi \cdot r^2 \cdot Q_{ext} \cdot n_d \qquad \text{Equation (7)}$$

Herein, r denotes the radius of the nanoparticle, $Q_{ext}$ denotes the efficiency of extinction and $n_d$ denotes the density of the nanoparticles in the article; in particular in the portion of the article, which is transmitted by light. After the efficiency of extinction $Q_{ext}$ has been calculated based on the infinite series according to the Mie theory, the efficiency of extinction τ may be obtained; and by using equation (3) the extinction of the article may be obtained in the at least one light transmissive portion, in which nanoparticles are dispersed. The extinction therefore linearly depends on the path D, through which light has been transmitted through the articles. For nanoparticles, which are made of gold, which have a concentration of $n_d = 7.0 \cdot 10^8$/ml and a radius of r=100 nm and further in case of a given sensitivity of 108 decibel (dB) of the OCT system 1, and a maximum extent D of the articles in the light transmissive portion in which the nanoparticles are dispersed of $D_{max} = 32$ cm results. According to equation (7) above in combination with equation (3) above, at a density, which is 10 times higher, i.e. $n_d = 7.0 \cdot 10^9$/ml, a value of $D_{max} = 3.2$ cm results.

Based on this description, the person skilled in the art is able to determine from a given sensitivity of the OCT system, a given geometry of the article, some or all of the relevant properties of the nanoparticles, such as material, extent, concentration, etc. such that equation (6) is fulfilled. Thereby, structures of the area of examination, which are located downstream of the article and in the beam path of the bundle of OCT measuring light 16, are detectable by the OCT system 1.

Furthermore, based on the size, structure and/or concentration of the particles, characteristics of backscattering of the nanoparticles may be determined by using suitable calculations. Thereby, by adapting the parameters of the nanoparticles, a higher reflectivity of the nanoparticles may be achieved for an improved detection by the OCT system.

The tweezers 41 comprise two legs 41a and 41b which can be moved towards and away from each other, such that teeth which are located in the jaws 42a and 42b may grab and hold tissue by applying a pressing force. The legs 41a and 41b comprise glass or plastics as a substrate and nanoparticles 26 which are dispersed in the volume having a concentration of about $n_d = 7.0 \cdot 19^8$/ml. In a method for using the tweezers 41 and by applying the OCT system 1, which is illustrated in FIG. 1, the tweezers 41 are imaged and the spatial orientation and position relative to the surrounding tissue of the eye 2 is determined. Thereafter, a correction of structure information which represent anatomical structures which are located downstream of the tweezers 41 is applied, in analogy to the correction method which has been described referring to FIG. 2.

The tweezers, which are schematically illustrated in FIG. 3 may be used for epiretinal membrane peeling. Tissue of the retina, is peeled using the tweezers, wherein an accurate positioning of the tweezers in relation to the epiretinal membrane is possible by imaging with the OCT system. In particular, a distance between the tweezers and the epiretinal membrane may be determined by using the OCT system.

Figure 4:
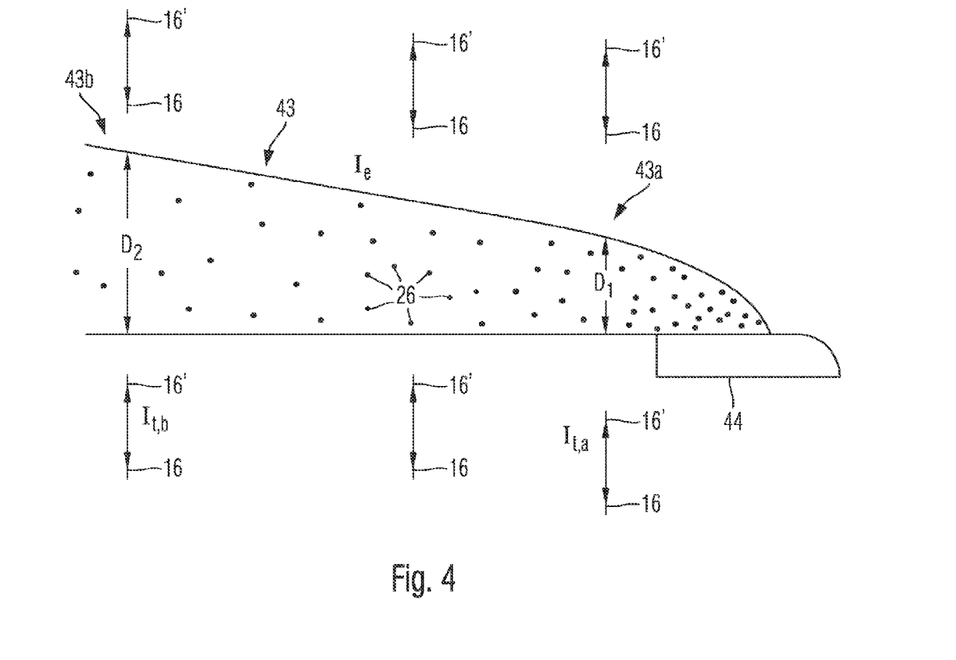
FIG. 4 illustrates an article, which is a scalpel according to an embodiment.

FIG. 4 illustrates a further embodiment of an article 43, which is used in a method which makes use of the OCT system 1. The article 43 is configured as a surgical scalpel, which comprises a metal plate 44 in a portion 43*a*. The substrate body of the scalpel 43 is made of a transparent material like plastics or glass and comprises a section 43*a* having a smaller cross-sectional extend $D_1$ and a section 43*b* having a greater cross-sectional extent $D_2$. In the substrate body of the scalpel 43, nanoparticles are distributed, having a higher concentration in the section 43*a* than in the section 43*b*. The inhomogenous concentration of the nanoparticles 26 in the sections 43*a* and 43*b* is chosen such that an extinction along a transmission direction defined by the direction of the bundle of OCT measuring light 16 in the section 43*a* is substantially equal to an extinction in the portion 43*b*. Thereby, it is ensured, that an intensity $I_{t,a}$ of OCT measuring light 16, which is transmitted through the section 43*a* is substantially equal to an intensity $I_{t,b}$ of OCT measuring light 16, which is transmitted through the section 43*b*, i.e. $I_{t,b}=I_{t,a}$. Thereby, structures of the eye 2, which are located downstream of the scalpel 43 may be imaged substantially with the same signal to noise ration, independent of a position along a direction of longitudinal extent, which is in this case approximately perpendicular to the transmission direction of the scalpel 43.

Figure 5A:
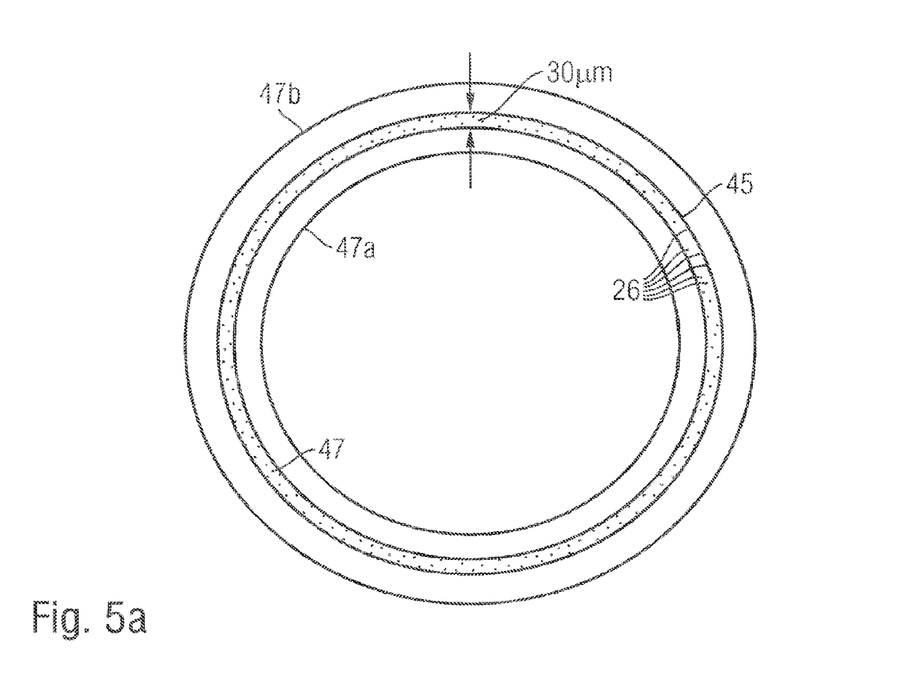
FIG. 5a illustrates an articles, which is a surgical thread according to an embodiment.

FIG. 5*a* schematically shows a further embodiment 45 of the article, which may be used in combination with the OCT system 1, which is illustrated in FIG. 1. The article 45 is a surgical thread, which may be inserted into the Schlemm's canal 47 of a human eye during an eye surgery. The surgical thread may in particular be used in combination with the method of viscocanaloplasty, wherein a liquid is injected for extending the Schlemm's canal.

The Schlemm's canal, which is limited in the cross-sectional view of FIG. 1 by lines 47*a* and 47*b*, and which is denoted in FIG. 1 by reference sign 47, contributes to the fluid regulation of the anterior chamber of the eye between the iris and the cornea. During an eye surgery, the tread 45 may be inserted into the Schlemm's canal 47, 47*a*, 47*b*. Thereby, either the geometry of the Schlemm's canal, which is otherwise only difficult to be imaged, may be determined or the Schlemm's canal may be deformed in a suitable way, for example by stretching. For increasing the contrast of the image generated by the OCT system 1, the surgical thread 45, which is made of a material such as Prolene comprises nanoparticles 26 which are deposited on the surface of the surgical thread by dipping the thread of Prolene into a solution of nanoparticles having a concentration of $7 \cdot 10^8$ nanoparticles per ml. The thread of Prolene 45 has a cross-sectional diameter of about 30 μm.

Figure 5B:
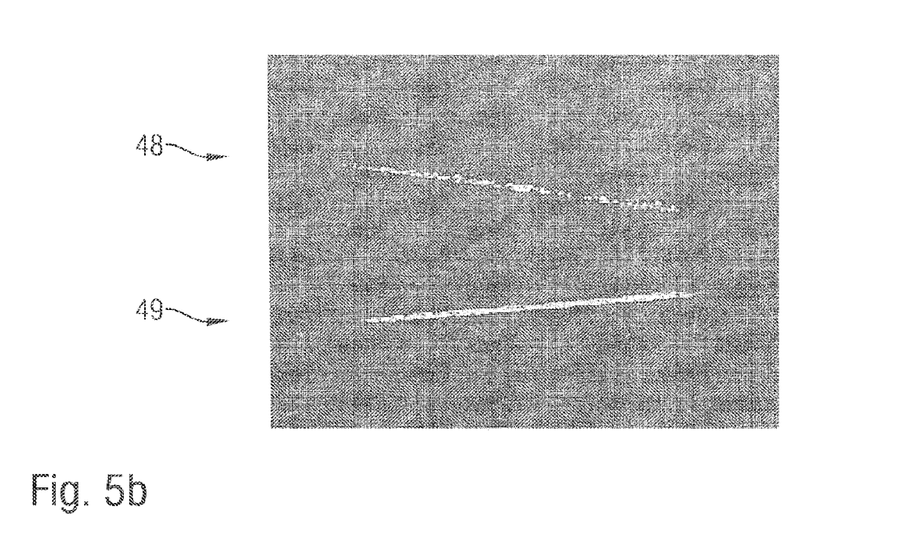

FIG. 5*b* illustrates results of two OCT measurements, wherein in the upper portion, there is shown a thread of Prolene without nanoparticles and in the lower portion, there is shown thread of Prolene with nanoparticles as described above, wherein the thread of Prolene is imaged by an OCT system 1 as shown in FIG. 1. The upper image 48 of the thread of Prolene without nanoparticles shows a lower signal which makes it difficult to obtain an accurate image of the thread for determining its position. In contrast thereto, the lower image of the thread of Prolene, in which nanoparticles are dispersed, has a signal which is higher by a factor of four than in the upper image 48. Thereby a more accurate measurement or a more definite manipulation of the Schlemm's canal during an eye surgery is possible by using an OCT system.

Other articles according to embodiments comprise portions of surfaces, which are provided with one or more layers which increase a reflectivity or which are roughened through a process, for increasing the imageability of the surfaces by an OCT system.

Figure 6A:
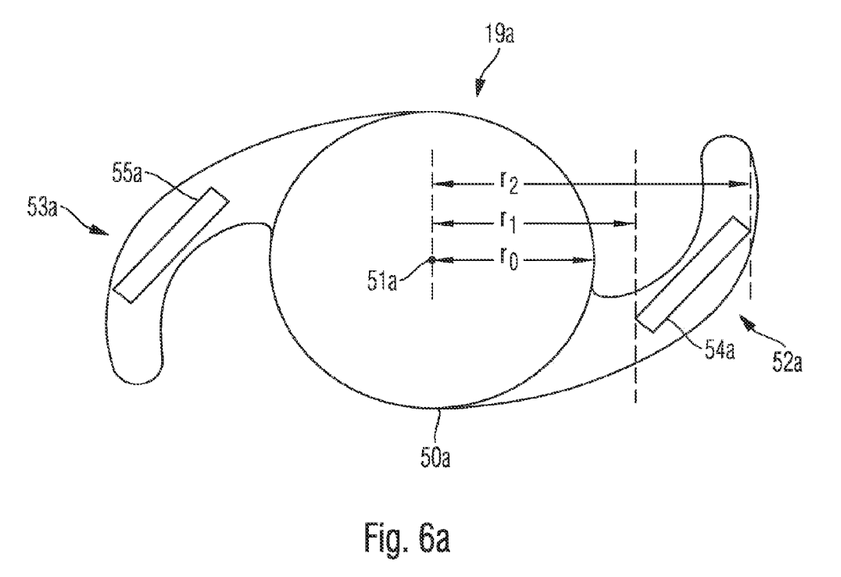
FIG. 6a shows an intraocular lens according to an embodiment.
Figure 6B:
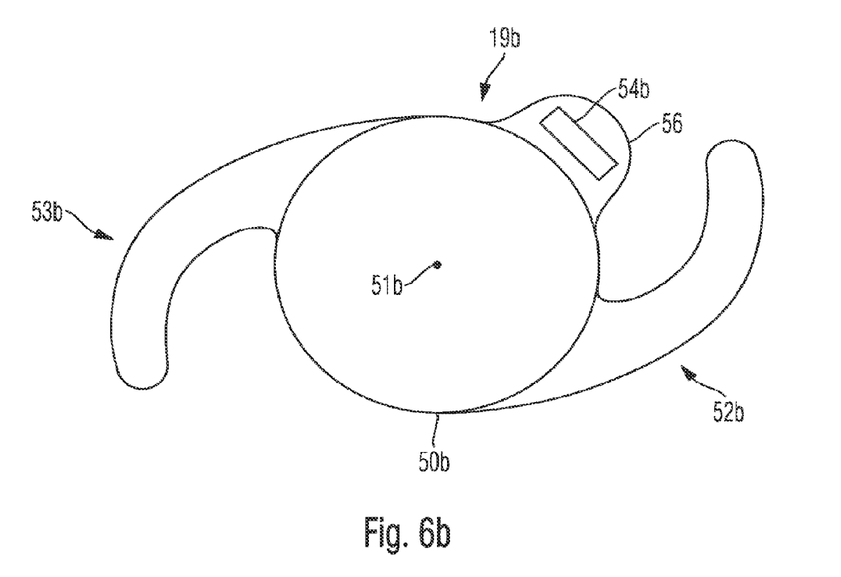
FIG. 6b shows an intraocular leas according to an embodiment.

FIGS. 6*a* and 6*b* schematically illustrate in a top view embodiments of an intraocular lens. The intraocular lens 19*a*, which is shown in FIG. 6*a* comprises an optical element 50*a*, which is substantially transparent in the visible wavelength range. The optical element 50*a* has a positive refractive power and an optical axis 50*a*, which is perpendicular to the drawing layer. The optical element 50*a* may be a spherical and/or toric lens.

Furthermore, the intraocular lens 19*a* comprises two holding elements 52*a* and 53*a*, which extend from inside to outside in a radial direction and which serve to hold the intraocular lens 19*a* in the capsular bag 17 of the human eye 2. At the holding element 52*a*, there is provided a mark 54*a* and at the holding element 53*a*, there is provided a mark 55*a*. The mark 54*a* or 55*a* may for example comprise a reflecting foil and/or information on optical properties of the intraocular lens 19*a*, treatment data, patient data and the like. The mark 54*a* or 55*a* may for example comprise characters or a barcode and information about an alignment of the main axis of the optical elements 50*a* in case it is a toric optical element.

The optical element 50*a* has a radius $r_0$ which defines a circular area, in which the optical power of the optical element 50*a* has a positive refractive power. The marks 54*a* and 55*a* are located outside of the circular area defined by the radius $r_0$, in a portion between the radii $r_1$ and $r_2$. The radii $r_1$ and $r_2$ are chosen under consideration of the anatomy of the eye 2 which is to be examined. In particular, it has to be ensured, that the intraocular lens 19, which is inserted into the capsular bag 17 is held within the capsular bag 17 by the holding elements 52*a* and 53*a* and bather that the marks 54*a* and 55*a* are located along an optical axis of the eye behind (i.e. downstream) of the iris, without limiting the field of view of the eye. For example, $r_1$ may be chosen to be greater or equal to 3 mm and $r_2$ may be chosen to be smaller or equal to 6 mm.

The intraocular lens 19*a* may be used for an improved cataract surgery by using the OCT system 1, which is illustrated in FIG. 1. Thereby, the high sensitivity of the OCT system 1 may be used for imaging marks 54*a*, 55*a* of the implanted intraocular lens 19*a*, which is located in the capsular bag 17 behind the iris 14, whereby it is possible to determine the exact position of the intraocular lens 19*a* within the capsular bag 17. An inaccurate position or inaccurate orientation of the implanted intraocular lens 19*a* may be determined, for example a tilt of the optical axis 51*a* of the intraocular lens 19*a* in relation to an optical axis of the eye or an inaccurate azimuthal orientation of the intraocular lens 19*a* relative to the optical axis 51*a* in case the optical element 50a is a toric optical element, the orientation of which is given by a main axis. An accurate positioning of an intraocular lens has been difficult by using common imaging systems and common intraocular lenses.

FIG. 6b illustrates a further embodiment 19b of an intraocular lens. Such as the intraocular lens 19a, which is illustrated in FIG. 6a, the intraocular lens 19b, which is illustrated in FIG. 6b comprises an optical element 50b having an optical axis 51b and two holding elements, which are located outside of the optical element 50b in a radial direction for holding the intraocular lens 19b in the capsular bag of a human eye 2. Contrary to the intraocular lens 19a, which is illustrated in FIG. 6a, there are provided no marks on the holding elements 52b and 53b. Instead, a mark 54b is provided on an outwardly directed portion 56, wherein the outwardly directed portion 56 extends in a direction from inside to outside of the optical element 50b in a radial direction. Other embodiments of intraocular lenses comprise further marks on the holding elements or further supporting elements, such as outwardly directed portions. The marks max comprise nanoparticles, which are arranged within a volume or a surface of a corresponding supporting element.

In addition to the articles as described above, other commonly used items or items which, are necessary in a surgery may be provided with nanoparticles, such as visco elastic materials, rinsing liquids, catheters or the like. Liquids, which contain nanoparticles, may be used to increase the contrast after having been injected into a tissue which is examined during being imaged by an OCT system. Liquids containing nanoparticles, such as visco-elastic materials may for example be injected into the anterior chamber of the eye or posterior chamber of the eye or into the Schlemm's canal for increasing contrast.

Figure 7A:
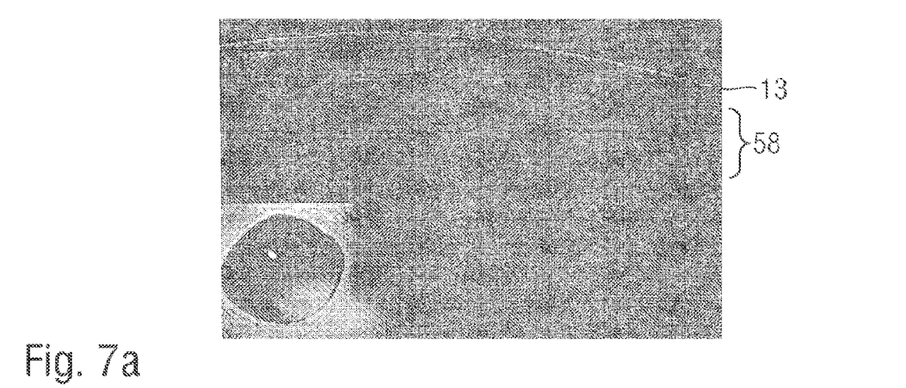
FIG. 7a shows results of OCT measurements according to an exemplary embodiment of a method.
Figure 7B:
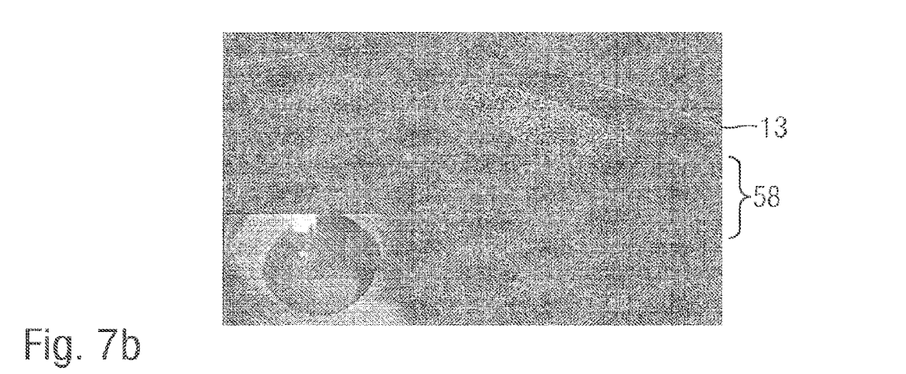
FIG. 7b shows results of OCT measurements according to an exemplary embodiment of a method.
Figure 7C:
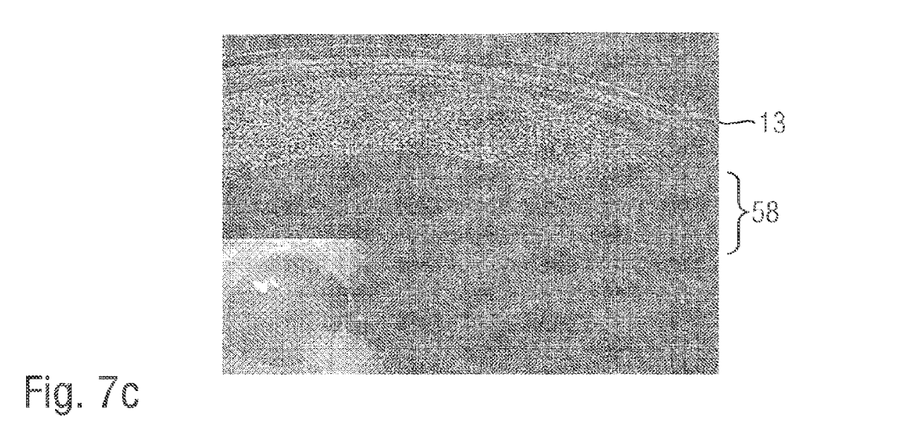
FIG. 7c shows results of OCT measurements according to an exemplary embodiment of a method.

FIGS. 7a, 7b and 7c illustrate the use of a liquid, which contains nanoparticles for increasing the contrast of the image of the anterior chamber of a trout's eye by using an OCT system. FIG. 7a shows an image obtained by an OCT system, which is illustrated in FIG. 1, of a trout's eye, wherein in the image which is inserted in the lower left corner, the eye of the trout is shown in top view. The image in FIG. 7a of the natural eye of a trout shows the outer limit of the cornea as a line 13, whereas the anterior chamber of the eye which is located below seems to have no limiting structures below the cornea.

FIG. 7b shows an image of the same eye of the front shortly after an injection of a liquid, which contains nanoparticles below the cornea. Portions within the anterior chamber of the eye, which are enriched with the liquid which contains nanoparticles, show an increased OCT signal.

FIG. 7c shows an increased OCT signal after a short time of waiting in a band 58 below the cornea 13, which is generated by reflection of the OCT measuring light at the nanoparticles. The fact, that the liquid, which contains nanoparticles has only spread out within a limited band, indicates that the anterior chamber of the eye is limited by structures below the cornea 13, which has not been recognizable in images of the natural eye of the trout. Thereby, using liquids containing nanoparticles which are injected into a tissue to be examined, an improved examination of this tissue is made possible.

An injected liquid which contains nanoparticles may be used together with articles according to FIGS. 2 to 5a and FIGS. 6a and 6b during an examination by an OCT system. Thereby, examinations and surgeries may further be improved.

While the invention has been described with respect to certain exemplary embodiments thereof, it is evident that many alternatives, modifications and variations will be apparent to those skilled in the art. Accordingly, the exemplary embodiments of the invention set forth herein are intended to be illustrative and not limiting in any way. Various changes may be made without departing from the spirit and scope of the present invention, as defined in the following claims.

What is claimed is:

1. An article for use in an OCT method, the article comprising:
   a solid substrate, having at least one light transmissive portion, which is light transmissive at least along a transmission direction,
   nanoparticles, which are, in the light transmissive portion, dispersed in and/or on the substrate;
   wherein the nanoparticles are configured and dispersed such that the nanoparticles result in an increased extinction of the light transmissive portion, compared to the substrate free of the nanoparticles, when measured along the transmission direction;
   wherein the extinction of the light transmissive portion, measured along the transmission direction, is less than 6,
   wherein the extinction is defined as a negative decadic logarithm of a ratio of an intensity of light which is transmitted through the light transmissive portion to an intensity of light which is incident on the light transmissive portion, and
   wherein the light is in a visible and/or in a near infrared wavelength range.

2. The article according to claim 1, wherein in the light transmissive portion, an extinction of the substrate when the substrate is free of the nanoparticles, is below 2, when measured along the transmission direction,
   wherein the extinction of the substrate is measured using the light in at least one of the visible and the near infrared wavelength range.

3. The article according to claim 1, wherein a reflectivity of the article in at least a portion of the light transmissive portion is increased by at least 0.1% compared to the substrate free of the nanoparticles;
   wherein the reflectivity is measured using the light in the visible and/or infrared wavelength range.

4. The article according to claim 1, wherein the article comprises a reflective portion within the light transmissive portion, wherein a reflectivity of the reflective portion, measured along the transmission direction, is greater than $10^{-10}$,
   wherein the reflectivity of the reflective portion is measured using the light in the visible and/or the near infrared wavelength range.

5. The article according to claim 1, wherein the nanoparticles cause an increase of the extinction of the light transmissive portion of at least $10^{-4}$ relative to the substrate free of nanoparticles.

6. The article according to claim 1, wherein the nanoparticles have an extent of between 1 nm and 100 μm or between 100 nm and 100 μm.

7. The article according to claim 1, wherein the nanoparticles comprise at least one of metal, silicon, oxygen and $AlO_3$.

8. The article according to claim 1, wherein a first concentration of the nanoparticles in a first subportion of the light transmissive portion is at least 2 times greater than a second concentration of the nanoparticles in a second subportion of the light transmissive portion.

9. The article according to claim 8, wherein the first subportion has a smaller transmission path length than the second subportion, measured along the transmission direction.

10. The article according to claim 1, wherein at least 80% of the nanoparticles are arranged on one or more surfaces of the substrate.

11. The article according to claim 1, wherein an extent of the light transmissive portion, measured along the transmission direction, is smaller than 20 mm.

12. The article according to claim 1, wherein the substrate comprises at least one of glass, plastics, and polymer material.

13. The article according to claim 1, wherein the article comprises a manipulator.

14. The article according to claim 13, wherein at least a portion of the light transmissive portion is an object engaging portion of the manipulator or is adjacent to an object engaging portion of the manipulator.

15. The article according to claim 14, wherein the object engaging portion is one of a tweezer jaw, an inlet end portion of a tube, and a tweezer leg.

16. The article according to claim 1, wherein the article comprises a surgical thread.

17. The article according to claim 1, wherein the nanoparticles comprise a core and a shell, wherein the shell surrounds the core.

18. The article according to claim 17, wherein the core comprises at least one of silicon and silicon oxide.

19. The article according to claim 17, wherein the shell comprises metal.

20. The article according to claim 1, wherein the nanoparticles comprise a metal, wherein the metal is one or a mixture of gold, silver, titanium, copper, cobalt, nickel, and iron.

21. The article according to claim 1, wherein the nanoparticles are biocompatible.

22. The article according to claim 1, wherein the light transmissive portion has a first and a second subportion which have different transmission path lengths, measured along the transmission direction;
wherein a concentration of the nanoparticles in the first subportion and a concentration of the nanoparticles in the second subportion are configured so that an extinction of the first subportion is substantially equal to an extinction of the second subportion, measured along the transmission direction.

23. The article according claim 1, wherein the article comprises a manipulator, wherein the manipulator comprises one or a combination of tweezers, a scalpel, and a tube.

24. The article according to claim 1, wherein the article comprises an implant.

25. The article according to claim 1, wherein the article comprises an intraocular lens.

26. The article according to claim 1, wherein the article comprises a synthetic thread.

27. The article according to claim 26, wherein the synthetic thread comprises Prolene.

28. The article according to claim 26, wherein the synthetic thread is configured to be insertable into a Schlemm's canal of an eye.

29. The article according to claim 26, wherein the synthetic thread has a thickness of less than 100 micrometers.

30. The article according to claim 26, wherein the nanoparticles are disposed on a surface of the synthetic thread.

31. The article according to claim 1, wherein the light enters the light transmissive portion through a first surface of the article and exits from the light transmissive portion through a second surface of the article.

32. The article according to claim 1, wherein the substrate free of nanoparticles has an index of refraction of substantially between 1.3 and 1.4 for the light.

* * * * *

UNITED STATES PATENT AND TRADEMARK OFFICE
CERTIFICATE OF CORRECTION

PATENT NO. : 9,554,701 B2
APPLICATION NO. : 14/265654
DATED : January 31, 2017
INVENTOR(S) : Wilzbach et al.

It is certified that error appears in the above-identified patent and that said Letters Patent is hereby corrected as shown below:

In the Specification

In Column 3, Line 62, delete "a least" and insert -- at least --, therefor.

In Column 4, Line 18, delete "articles," and insert -- article, --, therefor.

In Column 4, Line 33, delete "comprised" and insert -- comprises --, therefor.

In Column 8, Line 52, delete "dispersed" and insert -- described --, therefor.

In Column 9, Line 6, delete "the" and insert -- the visible --, therefor.

In Column 10, Line 2, delete "retracting" and insert -- refracting --, therefor.

In Column 10, Line 26, delete "an" and insert -- the --, therefor.

In Column 10, Lines 31-32, delete "In particular, the mark is arranged at smaller" and insert -- Furthermore, the distance is smaller --, therefor.

In Column 11, Line 49, delete "which" and insert -- with --, therefor.

In Column 11, Line 51, delete "articles" and insert -- article --, therefor.

In Column 11, Line 55, delete "articles," and insert -- article, --, therefor.

In Column 12, Line 9, delete "bar" and insert -- far --, therefor.

In Column 13, Line 26, delete "date" and insert -- data --, therefor.

Signed and Sealed this
Sixth Day of June, 2017

Michelle K. Lee
*Director of the United States Patent and Trademark Office*

CERTIFICATE OF CORRECTION (continued)

In Column 13, Line 54, delete "it" and insert -- its --, therefor.

In Column 15, Line 10, delete "handle" and insert -- bundle --, therefor.

In Column 15, Line 15, delete "measures" and insert -- measuring --, therefor.

In Column 15, Line 21, delete "fro," and insert -- from, --, therefor.

In Column 15, Line 46, delete "retraction" and insert -- refraction --, therefor.

In Column 16, Line 2, delete "articles" and insert -- article --, therefor.

In Column 16, Line 4, delete "nanoparticles" and insert -- nanoparticle --, therefor.

In Column 16, Line 12, delete ""MieCale"" and insert -- "MieCalc" --, therefor.

In Column 16, Line 37, delete "articles." and insert -- article. --, therefor.

In Column 16, Line 41, delete "articles" and insert -- article --, therefor.

In Column 16, Line 67, delete "$n_d=7.0 \cdot 19^8$/ml." and insert -- $n_d=7.0 \cdot 10^8$/ml. --, therefor.

In Column 17, Line 11, delete "peeled" and insert -- peeled by --, therefor.

In Column 17, Line 53, delete "tread 45" and insert -- thread 45 --, therefor.

In Column 18, Line 49, delete "bather" and insert -- further --, therefor.

In Column 19, Line 22, delete "max" and insert -- may --, therefor.

In Column 19, Line 46, delete "front" and insert -- trout --, therefor.

In the Claims

In Column 22, Line 11, in Claim 3, delete "according" and insert -- according to --, therefor.